United States Patent
Sasian et al.

(10) Patent No.: US 7,355,683 B2
(45) Date of Patent: Apr. 8, 2008

(54) SYSTEMS AND METHODS FOR EVALUATING AND DISPLAYING THE DISPERSION OF A DIAMOND OR OTHER GEMSTONE

(75) Inventors: Jose Sasian, Tuscon, AZ (US); James Caudill, Las Vegas, NV (US); Peter Yantzer, Las Vegas, NV (US); Jason Quick, Las Vegas, NV (US); Jason Flatt, Las Vegas, NV (US); Jacob Sheffield, Las Vegas, NV (US)

(73) Assignee: American Gem Society, Las Vegas, NV (US)

( * ) Notice: Subject to any disclaimer, the term of this patent is extended or adjusted under 35 U.S.C. 154(b) by 77 days.

(21) Appl. No.: 11/388,384

(22) Filed: Mar. 24, 2006

(65) Prior Publication Data

US 2007/0222972 A1   Sep. 27, 2007

(51) Int. Cl.
   *G01N 21/00* (2006.01)
(52) U.S. Cl. ...................................... 356/30
(58) Field of Classification Search ........ 356/30, 356/31
   See application file for complete search history.

(56) References Cited

U.S. PATENT DOCUMENTS

| | | | |
|---|---|---|---|
| 4,647,194 A | 3/1987 | Shigetomi et al. | |
| 5,118,181 A | 6/1992 | Yifrach et al. | |
| 5,164,586 A | 11/1992 | Hohberg et al. | |
| 5,196,966 A | 3/1993 | Yamashita | |
| 5,260,763 A | 11/1993 | Yamashita | |
| 5,430,538 A | 7/1995 | Kobayashi | |
| 5,615,005 A | 3/1997 | Valente et al. | |
| 5,627,638 A | 5/1997 | Vokhmin | |
| 5,966,673 A | 10/1999 | Shannon, Sr. | |
| 6,020,954 A | 2/2000 | Aggarwal | |
| 6,128,577 A | 10/2000 | Assa et al. | |
| 6,239,867 B1 | 5/2001 | Aggarwal | |
| 6,348,964 B1 | 2/2002 | Wagner et al. | |
| 6,567,156 B1 | 5/2003 | Kerner | |
| 6,665,058 B1 | 12/2003 | Gilbertson | |
| 6,795,171 B1 | 9/2004 | Gilbertson | |
| 6,980,283 B1 | 12/2005 | Aggarwal | |
| 7,136,154 B2 | 11/2006 | Bray | |
| 7,193,694 B2 | 3/2007 | Underwood | |
| 2002/0052170 A1 | 5/2002 | Holloway | |
| 2005/0190356 A1* | 9/2005 | Sasian et al. | 356/30 |
| 2005/0190357 A1* | 9/2005 | Sasian et al. | 356/30 |
| 2005/0200834 A1* | 9/2005 | Sasian et al. | 356/30 |
| 2005/0213077 A1* | 9/2005 | Sasian et al. | 356/30 |

(Continued)

OTHER PUBLICATIONS

"Software Plots Diamonds, Helps Identify Gems," Jewelers' Circular-Keystone, Oct. 1994.

(Continued)

*Primary Examiner*—Roy M Punnoose
(74) *Attorney, Agent, or Firm*—Lewis, Rice & Fingersh, L.C.

(57) ABSTRACT

Systems and methods for evaluating and displaying a diamond's dispersion or fire potential. These systems and methods can be used to determine the dispersion of a diamond relative to an observation point, which can then be used to provide for a map or other indicator of a diamond's fire potential when it is observed from that point.

20 Claims, 4 Drawing Sheets
(1 of 4 Drawing Sheet(s) Filed in Color)

U.S. PATENT DOCUMENTS

| | | |
|---|---|---|
| 2006/0074588 A1 | 4/2006 | Blodgett et al. |
| 2006/0164623 A1 | 7/2006 | Wagner et al. |
| 2006/0190292 A1 | 8/2006 | Reinitz et al. |
| 2006/0267975 A1 | 11/2006 | Moses et al. |

OTHER PUBLICATIONS

Sasian, Jose M., et al, "The Optical Design of Gemstones," Optics and Photonics News, Apr. 2003.

Solotaroff, Ivan, "Making the Grade," Modern Jeweler Magazine, Jun. 2005.

Yantzer, Peter, et al., "New AGS Cut Grading System," Rapaport Diamond Report, Jun. 3, 2005.

"The AGS ASET: A Real World View of Light-Handling Capabilities of a Faceted Diamond," www.kassoy.com/gemology/aset01.html.

Yantzer, Peter, et al., "New AGS Cut Grading System," www.rapaport.com/news/newsitem.asp?num=12383&type=all&topic-all&searchfor....

New Arrivals: Tools, Products and Services, Instore Magazine, Sep. 2005.

What Is the Ideal-Scope and What Does It Do?, www.pricescope.com/idealscope_indx.asp.

Russian Diamond Cut Studies, Diamond Calculator and Gem Adviser, www.pricescope.com/MSU/default.asp.

Diamond Calculator: Description, www.pricescope.com/MSU/diamcalc.asp.

Green, Barak, et al., "Diamond Appearance: The Components of a Computer Model," GIA Research, www.gia.edu/research/1383/431/article_detail.cfm.

Buck, Jamis, "The Recursive Ray Tracing Algorithm," www.geocities.com/jamisbuck/raytracing.html?200631.

Sivovolenko, S.B., Shelementyev, Y.B. and Holloway, G., "On grading the symmetry of a round brilliant cut diamond," Dec. 19, 2005, http://www.gemology.ru.cut/english/symmetry/_index.htm.

"Diamond Cut Study: Proposed Three Dimensional Modeling Method," http://www.gemology.ru.cut/english/conferens-article/_2.htm, printed May 30, 2006.

"Diamond Grading," Sarin Technologies LTD., http://www sarin.com/diamond.asp, printed May 30, 2006.

Bates, B., "Cut From the Same Cloth," JCK—Jewelers Circular Keystone Magazine, Jun. 2003.

"A JCK Exclusive: AGS and Eightstar sign research and development agreement," JCK—Jewelers Circular Keystone, http://www.jckgroup.com/index.asp?layout=articlePrint&articleID=CA227219&webzine=jck&p .., printed on Jun. 19, 2003.

Reinitz, I, Johnson, M. and Gilbertson, A, "Comments on the GIA Analysis of Diamond 'Fire,'" Letters, Gems & Gemology, Summer 2002.

* cited by examiner

SYSTEMS AND METHODS FOR EVALUATING AND DISPLAYING THE DISPERSION OF A DIAMOND OR OTHER GEMSTONE

BACKGROUND

1. Field of the Invention

This disclosure relates to the field of grading gemstones; particularly to systems or methods for evaluating and displaying the fire potential or dispersion of a diamond.

2. Description of the Related Art

Diamonds have traditionally been graded based on what is known as the four C's: color, clarity, carat weight, and cut. Other than carat weight which is directed to the actual size of the stone, the other three factors attempt to quantify or rank diamonds which are objectively better than others. The parameters, therefore, are ways of indicating how light interacts with the diamond, whether the stone appears bright and lively, and whether the diamond appears to produce color or not.

While the four C's have a long standing tradition, they are, in many respects, a stand in for what is a subjective appearance to a user. Instead of talking about more objective grading standards, many users instead will focus on what they see in a diamond. This may relate to color or to "liveliness" of a diamond. A well cut diamond, when moved, will often appear to include many different colors of light in a number of different locations making the stone have what appears to be a large amount of internal movement, color, and prismatic effect.

Generally, a diamond's effect on light is characterized by referring to the stone having fire, brilliance, or scintillation. All of these terms relate to the stone's ability to reflect, refract, or otherwise act on incoming light in a particular fashion. Brilliance is generally the stone's ability to redirect white light toward a viewer, scintillation is generally the apparent movement or flashing of light in the stone, and fire is generally the ability of the stone to disperse light and produce colors which appear to be within the stone.

Interestingly, cutting a diamond for one effect will often lower the ability to see other effects. For instance, a very brilliant diamond, will often appear to not have much fire. While color may be being produced and the stone does produce a high level of dispersion, the color may be washed out by the high level of white light. Therefore, it often requires examination of a stone under many different lighting conditions to see its true attributes.

Because of the complexity of a diamond's geometry as well as the different kind of environments in which it may be viewed, purchasing diamonds is often very hard on a consumer. They may look at a diamond and think it is attractive, but are concerned that what they like is not objectively "better" or that they are being overcharged for an item which is as much an investment as a purchase. For this reason, an ability to objectively evaluate and also to more systematically explain and display the properties of a particular diamond are desirable.

SUMMARY

Because of these and other problems in the art, described herein, among other things, are systems and methods for evaluating and displaying a diamond's dispersion or fire potential when viewed from a particular location. These systems and methods can be used to quantify the dispersion of a diamond, which can then be used to provide for a map or other indicator of a diamond's fire potential which provides for a methodology to compare the fire potential of different stones.

Described herein, is a method for evaluating the fire potential of a gemstone, the method comprising; generating a representation of the geometry of a gemstone having a table and a plurality of faces; defining a target point above the table of the gemstone; tracing a first ray of a ray pair having a first wavelength from the target point through the gemstone allowing the first ray to interact with at least a portion of the faces; determining a source point at which the first ray intersects a first surface after leaving the gemstone; tracing a second ray of a ray pair having a second wavelength from the source point and through the gemstone allowing the second ray to interact with at least a portion of the faces; determining an intersection point at which the second ray intersects a second surface; calculating a dispersion between the first ray and the second ray; repeating the above steps for a plurality of ray pairs; and using the dispersions to evaluate the fire potential of the gemstone.

In an embodiment of the method, the gemstone is a diamond. the step of calculating may comprise determining the distance of the target point to the intersection point, the distance may be within a predetermined range of distances, the range being one of a plurality of ranges of distances. The step of using in this method may comprise the steps of: color coding each of the predetermined ranges in the plurality; providing a graphical view of the table of the gemstone; and mapping the color coding associated with the range associated with the distance on the location of the graphical view of the table that the first ray intersected the table, the table may be part of a crown and wherein the step of using comprises the steps of color coding each of the predetermined ranges in the plurality; providing a graphical view of the crown of the gemstone; and mapping the color coding associated with the range associated with the distance on the location of the graphical view of the crown that the first ray intersected the table.

In another embodiment of the method the first ray enters the gemstone through the table, the first surface is a hemisphere, and the second surface is a plane.

In another embodiment of the method the portion of the faces with which the second ray interacts is the same portion of faces with which the first ray interacts. The second ray may interact with the portion of the faces in the opposite order that the first ray interacts with the portion of the faces.

There is also discussed herein a system for evaluating the fire potential of a gemstone the system comprising: a computer having software running thereon, the software being able to generate a representation of a gemstone in a computer readable form; an algorithm operating on the computer for tracing a ray through the representation of the gemstone to form a path; and a memory for storing the path; wherein, a first path is traced for a first ray having a first wavelength and originated at a target point, the first ray also intersecting a first surface at a source point after being traced through the representation; wherein a second path is traced for a second ray having a second wavelength and originated at the source point, the second ray not intersecting the target point after being traced through the representation; wherein the computer can calculate a dispersion associated with the ray pair including the first ray and second ray based on the first path and the second path; and wherein the computer can repeat tracing first paths, tracing second paths, and calculating an associated dispersion for a plurality of ray pairs.

In an embodiment of the system the gemstone is a diamond and the first surface is a hemisphere. In another embodiment, the computer can also provide a representation of all the dispersions, the representation indicating the fire potential of the gemstone. The representation may be alphanumerical or graphical.

There is also discussed herein, a method for indicating the fire potential of a gemstone, the method comprising: providing a graphical representation of at least a portion of a surface of a gemstone; defining a target point, a plurality of source points and a plurality of contact points, each contact point in the plurality of contact points being on the portion of the surface of the gemstone; calculating that white light sourced at one of the source points and directed into the gemstone is dispersed a particular distance by the gemstone and that light of a first predetermined wavelength sourced at the same source point and directed into the gemstone follows a first trace which passes through a first of the contact points and through the target point; selecting at least two different indicators, each of the indicators representing a particular range of distance of dispersion; recognizing which of the ranges of distances of dispersions includes the distance of dispersion of white light sourced from the first of the source points; placing the indicator representing the range of distance of dispersions including the distance of dispersion of white light sourced from the first of the source points on the graphical representation at the contact point; repeating the steps of determining, selecting, recognizing and placing for all of the contact points; and utilizing the resultant graphical representation as an indicator of fire potential of the gemstone.

In an embodiment of the method the indicators are colors, the step of calculating the particular distance is calculated by generating a ray pair via reverse ray tracing, wherein one of the rays in the ray pair follows the first trace, or in the step of calculating, the particular distance is calculated by generating a ray pair via forward ray tracing, wherein one of the rays in the ray pair follows the first trace.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

DESCRIPTION OF PREFERRED EMBODIMENT(S)

The value of a diamond generally depends first on its size, but next on its appearance. The appearance of any stone necessarily depends on factors intrinsic to the raw diamond, such as the clarity of the stone, and whether the stone includes any flaws in its crystalline structure. However, the appearance of a diamond or any other gemstone which is intended to be used as an artistic optical structure will also depend greatly on its cut. A skilled diamond cutter can transform a raw diamond into a beautiful optical structure that interfaces amazingly with light.

While all these intrinsic factors of a diamond affect its appearance and, therefore, its quality and value, a diamond's appearance in any given situation also depends on extrinsic factors, such as how the diamond is illuminated and how it is observed. Many jewelers utilize high intensity light to show off their best stones. While this can be a good indicator of a stone's brilliance, it often results in a stone's other features being covered up. This can be particularly important in the purchase of diamond jewelry where the lighting of the stone when it is worn may be quite different from the lighting when it is purchased.

Figure 1:
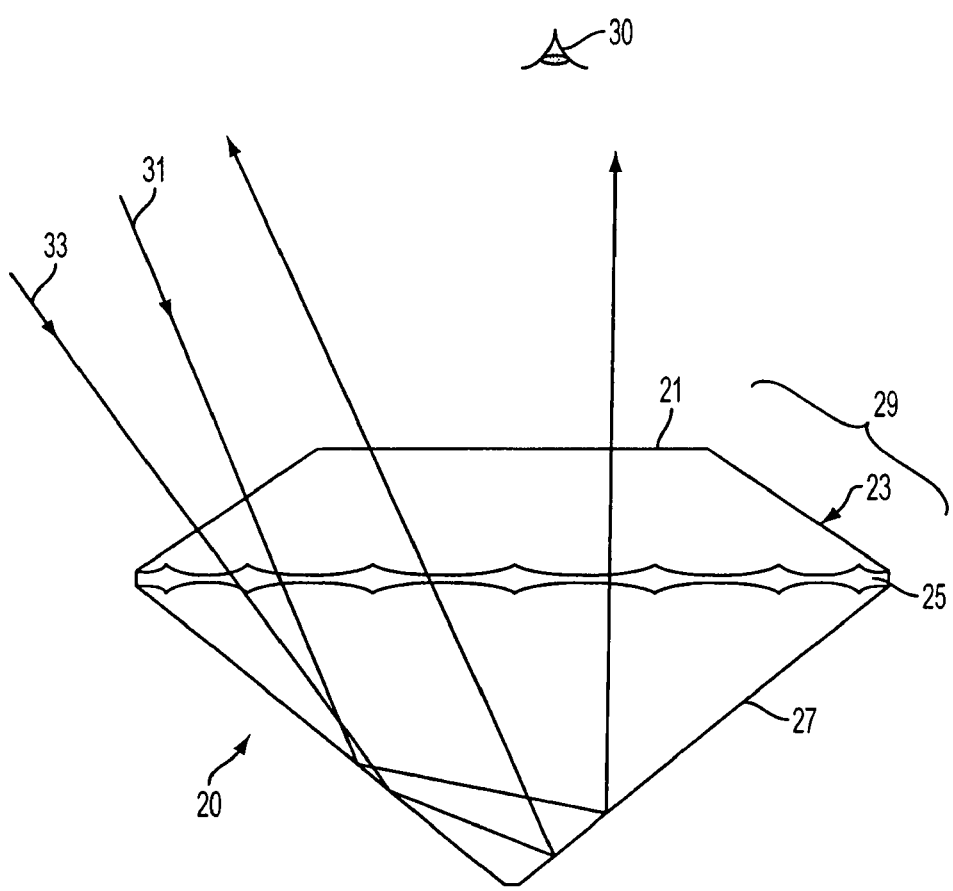
FIG. 1 shows a cross sectional view of a brilliant round cut diamond showing light rays incident thereon.

In a diamond, only the cut can be controlled by human intervention, and therefore the ability to know how to cut a diamond to provide the best look possible for any particular raw stone is of paramount importance to those who create diamond jewelry. In FIG. 1 there is shown a two dimensional wire frame representation of a diamond (20). The cut of a diamond (20) refers to not only the diamond's shape (e.g., diamond (20) is a brilliant round cut diamond as opposed to an oval or princess cut), but also to the relative proportion and orientation of the different portions of the diamond (20). A well cut diamond is cut to a particular shape, as well as having the various dimensions of that shape be to exacting relationships. These relationships are intended to allow the diamond to interact with light in what is generally seen as the most evocative manner possible. A well cut diamond is essentially a very complex optical structure, which is much of what gives it its appeal.

When referring to a diamond (20), there are a number of facets of its geometric structure which create its form and, therefore, its optical effect. Obviously, it is generally not possible to cut inside the diamond's form. The shape, size, and spacing of external faces, however, can dramatically improve, or hinder, the diamond's ability to act as an optical structure in a desirable fashion. Parts of a cut diamond generally include the table (21), bezel (23) (which combined form the crown (29)), girdle (25), and pavilion (27). All of the angles associated with these components, as well as the actual precision of the cuts themselves combine to make a diamond of a better cut.

The purpose of the various facets is to obtain a dynamic interaction with light when the stone is viewed. In a typical desired viewing situation the diamond is facing an observer (30), and the observer (30) is "above" the diamond (20) and looks generally into the table (21) and into the stone. Diamonds are generally cut to be observed in this fashion as observation from this direction allows the most interesting optical features to be observed.

Most jewelry designs place the diamond (20) in a mounting to allow for it to be observed in this way by placing the users body "below" the diamond (20). When the diamond (20) is viewed, light, such as rays (31) and (33) enter the diamond (20). These may be through the crown (29) or through the pavilion (27). The rays (31) and (33) are then internally reflected until they are finally directed toward the observer (30) or elsewhere. If directed toward the observer (30), the rays will add brilliance or fire to the diamond (20) If directed elsewhere, they have little to no positive effect on the stone's appearance from that position.

The optical function of a diamond's (20) cut includes bringing white light to an observer's (30) eye (which makes the gem appear to glow or shine and is usually referred to as a diamond's brilliance) and also in providing for prismatic effects so that incoming white light is dispersed and different colors of light are observed in the diamond (20) (which is often referred to as fire). The dispersion effectively provides color in what is actually a colorless stone because the interaction of different facets of the diamond's (20) geometry results in light of some wavelengths from a particular source being reflected toward the observer (30), while light of other wavelengths is reflected in such a way that it is not incident on the observer. This dispersion of light allows for color to be observed which appears to originate inside the diamond (20).

The problem with observing fire is that a brilliant diamond (20) will often direct so much white light toward an observer (30) that when the diamond (20) is viewed under the high power bulbs many jewelry stores use to show off the brilliance of the diamond (20), the diamond's (20) fire is concealed or buried in the white light. Viewing a diamond (20) under localized illumination is generally the best way to determine fire, something which is often not done when purchasing diamonds.

Therefore, the extent of both fire and brilliance observed in a diamond (20) depend on both the diamond's (20) cut proportions and on the illumination conditions under which the diamond (20) is observed. As it is often difficult for a purchaser to control illumination conditions in a purchasing situation, it is therefore desirable for there to be a convenient way to display the fire of the stone and compare one stone's ability to produce fire or brilliance with another. In this way two stones can be compared effectively under a multitude of lighting conditions, without having to actually look at them under those lighting conditions. In this application, the ability of a stone to disperse light, and therefore presumably produce fire under the right lighting conditions, is referred to as the stone's "fire potential." It should be realized that a stone with a high fire potential may not actually appear to have more fire to an observer because the fire may be buried in the stone's brilliance or other characteristics, however the stone has the potential to produce more fire under the right conditions, and may actually produce more fire, even if it cannot be seen. A user is provided with a display of fire potential to allow comparison of stones. The display will generally be graphical in nature providing a visual indicator of fire potential at a multitude of different points in the stone. In an alternative embodiment, however, the display may be alphanumerical or otherwise categorical to show a general indicator of the entire stone's fire potential at once.

U.S. patent application Ser. Nos. 11/018,042; 11/018,743; 11/018,742; and 11/018,744, the entire disclosures of which are herein incorporated by reference, provide for systems and methods for evaluating various properties of a diamond or other gemstone and provide for systems and methods for providing quantifiable relationships between different diamonds including various graphical representations of different aspects of a diamond or gemstone. This application goes into a method for evaluating and indicating the fire potential or dispersion of a diamond or other gemstone and can be used in conjunction with the systems, apparatus, and methods of those applications as well as on its own or with other related systems or methods.

Fire can be measured by measuring the relative dispersion, in the form of the angle of exit, of two rays of different wavelengths initiated at the same point source placed at the expected location of an observer (30). Based on simple geometry, these correspond to two rays of equivalent wavelength in the reverse direction. The greater the angle between the rays upon exiting the diamond and being detected at a detector representing the environment outside the observer, the greater ability for the diamond to disperse light. This is called reverse ray tracing because the rays traced are actually the "reverse" of rays that are incident on the eye and can be used in an embodiment to generate a fire potential map.

The problem with this system and the use of reverse ray tracing, is that it is not an entirely accurate indicator of fire potential from the point of observation. As should be apparent, if one was to shine light on the diamond (20) in the direction of the reverse of the rays (toward the observer (30) or tracing "forward") of the component wavelengths from the relative exit points, the light would actually combine when it reached the observer (30). In effect, this system shows the ability of the diamond (20) to combine disparate light from two different environmental sources making the combination incident on an observer (30). Fire, however, is observed when white light from a single environmental source is dispersed by the stone so that only a portion is incident on the observer (30). While the ability to combine can be used as an estimator for dispersion, it is not entirely accurate in all cases. Reverse ray tracing, however, has previously been computationally simpler than forward ray tracing because forward ray tracing has an extremely high number of potential point sources. In most cases this extreme number made the calculation prohibitively time consuming.

As fire relates to color, what the observer (30) is seeing will generally be a very complex interaction of light from multiple directions both diverging and converging on their eye. To put this in terms of simple physics, if light from a particular point source is dispersed widely by the cut of the diamond (20), white light incident from that particular point source may result in the observer (30) seeing a narrow color band as only those wavelengths are sent towards their eye while other wavelengths are bent sufficiently enough as to miss the observer's (30) eye at its current location. As the stone moves slightly to a second position, the high dispersion can still result in a narrow band of wavelengths being reflected to the observer's (30) eye, but the narrow band may be at a different point in the spectrum.

In order to quantify the fire potential of a diamond (20), the systems and methods discussed herein preferably measure the ability of a diamond (20) to disperse incident light directed on a path toward an observer (30) from a large number of different environmental point sources. The system indicates the dispersion present in any particular light path where some light is incident on the observer by measuring the angle that two different wavelengths of light from the same environmental point source exit the diamond (20). By providing that at least one of the wavelengths be incident on the observer (30), this path will provide some light to the observer when the diamond (20) is placed under general lighting conditions.

The evaluation process begins by first taking a representation of the diamond's (20) geometry, and then determining how light will pass through the diamond (20). The geometry can be generated computationally using, for example, commercially available optical design programs such as ASAP™ (available from Breault Research Organization, Tucson, Ariz.), FRED (available from Photon Engineering, Tucson, Ariz.), LightTools® (available from Optical Research Associates, Pasadena, Calif.), TRACEPRO® (available from Lambda Research, Littleton, Mass.) or ZEMAX® (available from ZEMAX Development Corporation, San Diego, Calif.).

Figure 2:
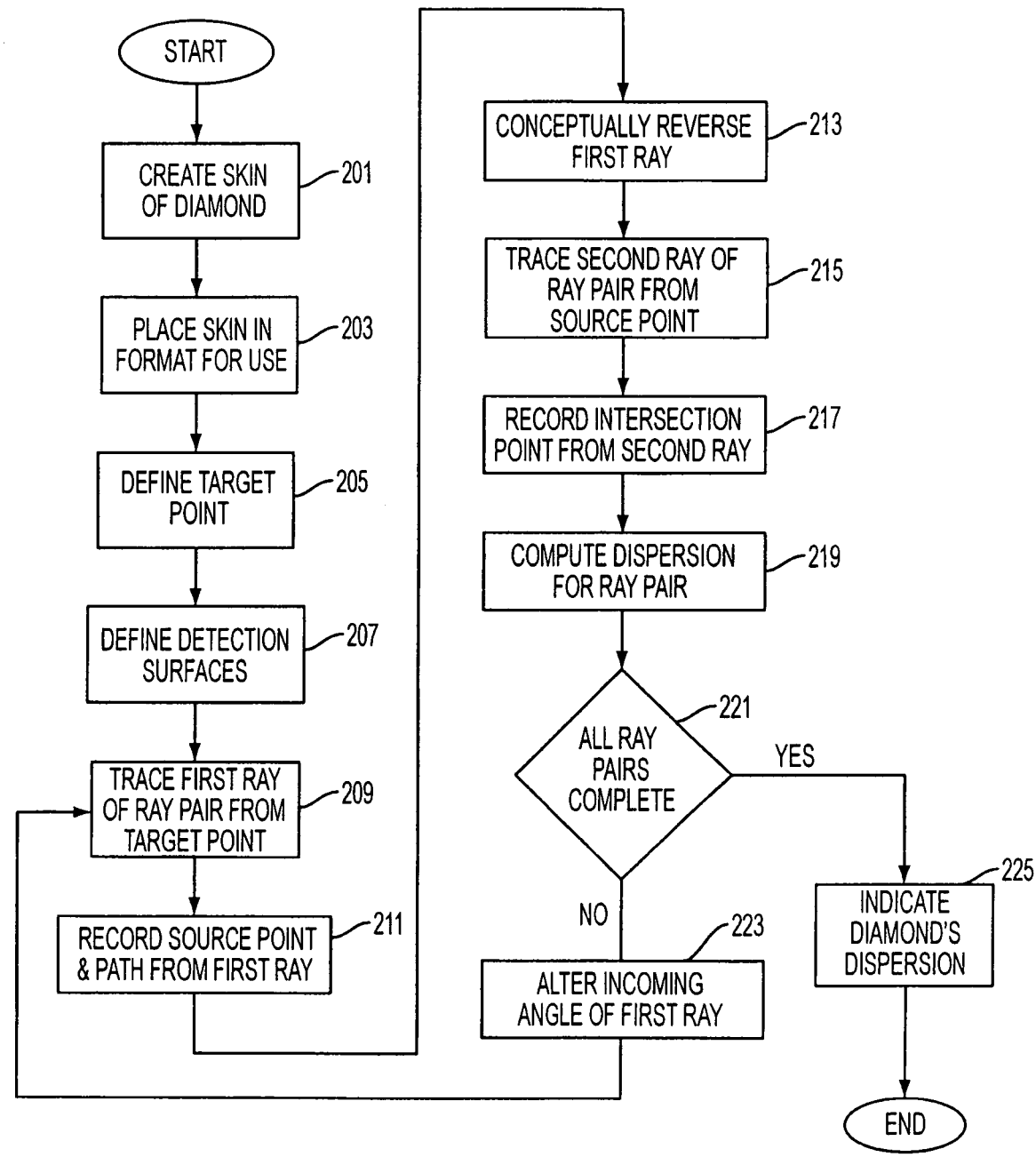
FIG. 2 shows a flowchart showing the steps of a method for measuring the dispersion of a diamond.

Referring to FIG. 2, a method for determining fire potential for light which leaves a particular portion of the diamond and is at least partially incident on the observer (30) is shown in flow chart form. In step (201) a "skin" of the diamond is created. A "skin" refers to a data set including information about the diamond's geometry, such as the size and shape of each facet, and facet angles and locations. A skin may be acquired using a DiaMension™ tool running DiaVision™ software, both available from Sarin Technologies Ltd. (Sarin USA, New York, N.Y.). Methods for obtaining a skin are understood by those of ordinary skill in the art. The skin is effectively a representation of the diamond which can be understood by a computer, processor, or other computational device which will now act upon it.

Once the skin is acquired, it is converted into a file format that can be used in an optical design program in step (203) so that ray paths representative of incoming light of different light waves and from different point sources can be determined and recorded. Again, this type of methodology is well understood to those of ordinary skill in the art.

Figure 3:
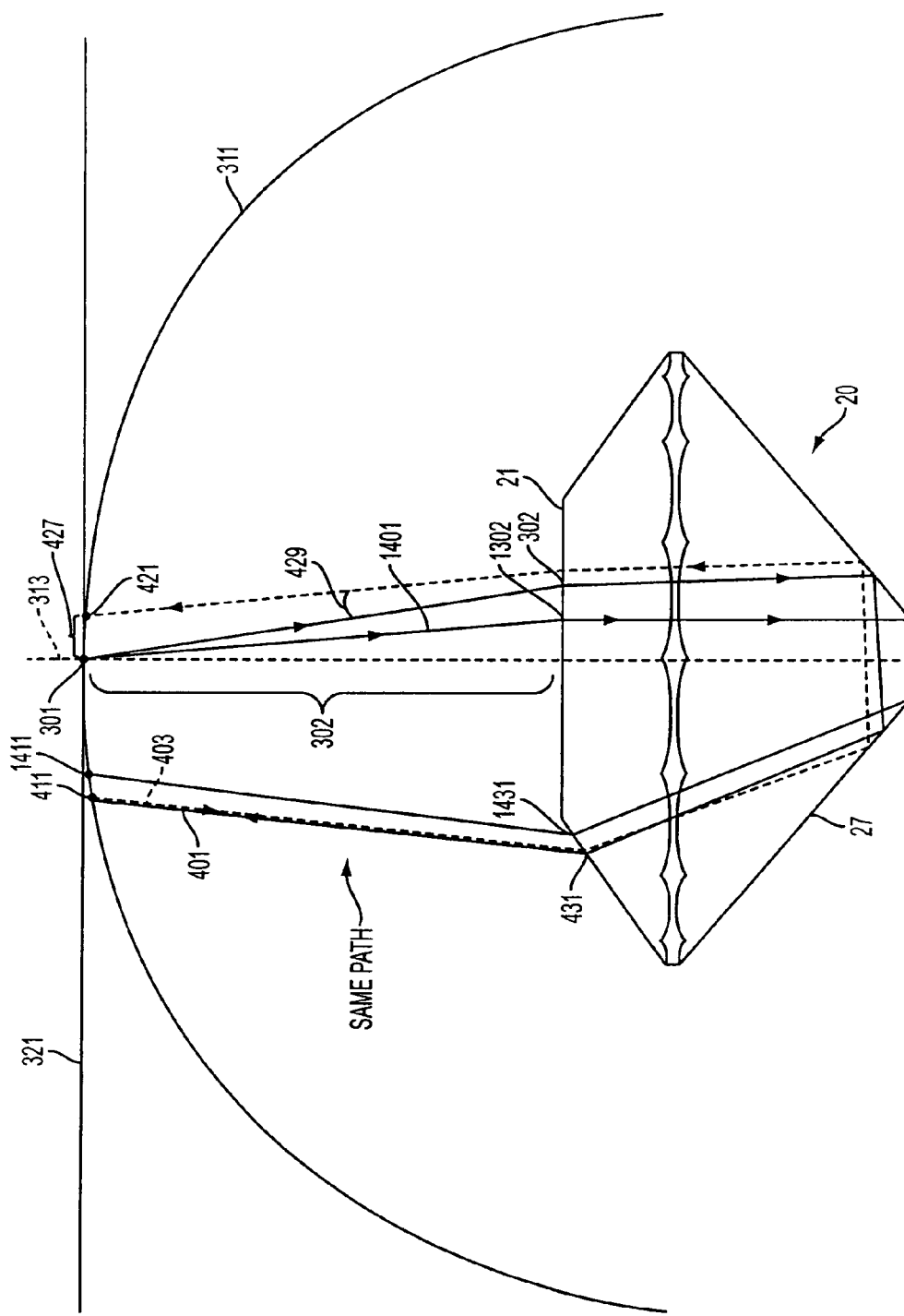
FIG. 3 shows a diamond with a ray pair formed of a first and second light ray showing dispersion in the ray pair. There is also showing a possible second first ray of another ray pair.

Prior to tracing ray paths through the diamond, the user defines a target point (301) in step (205). The target point (301) is a defined location which is effectively a stand in for the observer (30). The target point (301) is preferably located over the center of the table (21) of the diamond (20) at a first predetermined distance (302) as shown in FIG. 3. However, in alternative embodiments other locations can be used. The selection of target point (301) is based on how a hypothetical observer (30) is viewing the stone. In most cases the viewing is centered over the table to represent the "ideal" viewing location. However, other positions can be chosen to further show the properties of the diamond. The target point (301) will, therefore, correspond generally to the observer (30) and will be used where a wavelength is incident on the observer (30). The distance (302) between the target point (301) and the diamond (20) can vary. Typically, the target point (301) is located between about one centimeter and about 100 centimeters from the diamond (20), preferably between about 20 centimeters and 40 centimeters, and often at about 25 centimeters.

In an embodiment, more than one target point (301) can be used which would result in target points (301) at a plurality of distances and/or locations. In such an embodiment, an array of target points (301) will generally be used. The outcome of one such embodiment is shown by the various maps (707), (708), (709), (710), (711), (712), and (713) shown in FIG. 4 where the target point is slowly moved off center (the diamond is rotated) providing the array of target points (301). For simplification of discussion, however, a single target point (301) is selected in FIG. 2. The process discussed herein would generally just be repeated for each target point if multiple points were used. As should be apparent, FIG. 3 is drawn to show concept and should not generally be considered to be even remotely to scale.

In step (207) there are next defined surfaces (311) and (321) for the detection of incident rays. In general, the geometry of the surfaces (311) and (321) may vary as desired. In the depicted embodiment of FIG. 3, two surfaces (311) and (321) are used. The first surface (311) comprises a generally hemispherical surface centered on the diamond (20) and extending around the pavilion (27) as depicted in FIG. 3. First surface (311) preferably collects light rays in concentric rings at one degree angular spacing for a total of 90 rings but that is by no means required. The target point (301) is located at a pole (313) of first surface (311). The hemispherical shape of first surface (301) is in no way required and other shapes such as, but not limited to, parallelepipeds, planes, ellipsoids, hyperboloids, or paraboloids can be used. The purpose of this first surface is to locate a first point of intersection called a "source point"

(411) of a ray. The source point (411) is effectively a point in space representative of a potential source of a light ray whose dispersion path is desired.

In general, the radius of the hemisphere forming first surface (311) may vary as desired. For example, the radius of the hemisphere can be between about one centimeter and about 100 centimeters from the diamond (20), preferably between about 20 centimeters and about 40 centimeters, generally about 25 centimeters. In this example, the distance between the target point (301) and diamond (20) is the same as the radius of the hemisphere. However, in other embodiments, the distance between the target point (301) and diamond (20) may be different from the radius of the hemisphere.

The second detection surface (321) is preferably a planar surface. The second surface (321) passes through the target point (301) and is generally parallel to the table (21) of the diamond (20). The second surface (321) will preferably intersect the target point (301) and while a planar surface is generally preferred for simplicity, the second surface (321) can be of any shape, including being duplicative of first surface (311).

Once the target point (301) and detection surfaces (311 and 321) have been defined, a first ray (401) of a first prespecified wavelength is traced through the diamond in step (209). This first ray (401) originates from the target point (301) and will generally be directed into the diamond via the table (21) or bezel (23) but may be directed into the diamond at any position. The point of contact between the first ray and the diamond (20) is called the contact point (402) Once inside the diamond (20) the first ray's (401) interaction with the diamond (20) is computed by the processor by determining how the ray bounces from the diamond's various faces and eventually exits the diamond (20). After exit, the first ray (401) will travel in a straight line and intersect the first surface (311).

In this step (209), the first ray (401) is generally traced based on physical laws that describe the interaction of electromagnetic radiation with matter. This is often performed in a computer or other processor utilizing mathematical representations of recognized physical phenomena, which are often computerized into a control algorithm. For example, the algorithm can trace the first ray (401) based on Snell's law of refraction and/or the law of reflection, which predict the path of a ray at an interface between two media (such as diamond and air in this case). The algorithm can account for ray splitting, for example, due to Fresnel reflections at an interface between two media and may be able to account for multiple ray splitting, for example, due to higher order reflections. Regardless of the exact manner in which the first ray (401) is traced, the processor will eventually produce a representation of the path through the diamond (20) that the first ray (401) followed. As should be apparent, while the paragraph above discusses the ray having a wavelength, that is not expressly required as the identical result can be obtained by setting the index of refraction of the surfaces. As these are effectively interchangeable methodologies, both are intended to be included when discussing the ray having a wavelength.

In step (211), the intersection of the first ray (401) with the first surface (301) and the path of the first ray (401) through the diamond (20) are recorded. Generally, the path is recorded by recording the locations at which the first ray (401) intersected the facets or faces of the diamond (20) and the order in which the facets or faces were intersected. This order is often the more useful part of the trace and, in this disclosure, the path of the ray generally refers to the faces interacted with and the order in which the interaction occurred. FIG. 3 illustrates an exemplary first ray (401) which has started at the target point (301), been reflected various times by the diamond (20) and is now intersecting the first surface (311). This point of intersection is referred to as the source point (411) as previously discussed.

The source point (411) is important as it will now be the point source for incoming light into the diamond (20) whose dispersion is to be calculated. To do this, the first ray (401) can now be conceptually compared to the same wavelength of light being incident on the diamond (20) but being sourced from the source point (411) entering the diamond (20) along the straight line path which the first ray (401) left, bouncing around inside the diamond (20) by following the perfectly reverse trace of the first ray (401). Upon exiting the diamond (20) at the contact point (402), this reversed ray is incident to the target point (301). Therefore, the recorded trace indicates that light of the same particular wavelength as the first ray (401) sourced at the source point (411) and entering the diamond at the point (431) the first ray (401) left, will travel the same trace and will intersect the target point (301). To state this another way, the conceptual reversion of ray (401) not only follows the reversed path (order of faces intersected) but has the same trace (it is the reverse combination of vectors with the direction reversed). Now, as should be apparent, by centering the target point (301) over the table (21), this conceptually placed an observer's center of vision at the target point (301) and centered on the diamond (20). In effect, the ideal viewing angle. The system has also identified light of a particular wavelength that would be incident on the observer by being incident on the target point (301) from the source point (411).

This conceptual reversion of the first ray (401) takes place in step (213). One of ordinary skill in the art, however, would understand that the reversion of the first ray (401) is not something that has to actually occur, but is a conceptual step to point out that the first ray (401) that has been traced can represent light incident on the target point (301) from the source point (411) after passing through the diamond (20).

In step (215) a second ray (403) is now traced. This second ray (403) is initiated at source point (411) instead of at the target point (301). This second ray (403) will have a different wavelength from the first ray (401) but will be incident along the trace by which the first ray (401) left the diamond (20). That is, it will enter the diamond (20) at the point (431) where the first ray left. In effect the first leg of the trace of the reversed first ray (401) and the first part of the trace of the second ray (403) are identical. Upon the second ray (403) interacting with the diamond (20), the second ray will generally be bent differently to the first ray. This is shown in FIG. 3 by the divergence of the rays (401) and (403) after contact with the diamond (20). The second ray (403) is traced back through the diamond (20) until it also eventually leaves. In most cases, the second ray (403) will leave the diamond (20) through the table (21) of the diamond (20), but will not pass through the target point (301) if the path acts to disperse white light. It may or may not pass through the contact point (402). Instead, the second ray (403) will intersect the second surface (321) at an intersection point (421) separated from the target point (301) by a distance (427). Assuming that the second ray (403) does not pass through the target point (301), the path of light incident from the source point (411) shows at least some dispersion. Generally, this dispersion will create a triangle as shown in FIG. 3. The intersection point (421) and path of the second ray (403) will generally be recorded in step (217). As should be apparent from FIG. 3 while the rays (401) and (403) do not follow duplicate traces after they intersect the diamond (20), ray (403) follows the same path as the reversed ray (401). Conceptually, it should then be apparent that a spectrum of wavelengths including and between the wavelengths of the first ray (401) and second ray (403) will also follow the same path, however, they will be dispersed across the distance (427).

From the triangle of FIG. 3 it is possible to compute the angle of dispersion (429) of the path taken by the reversed first ray (401) and second ray (403) through the diamond (20). This computation is performed in step (219). The angle (429) computation step (219) may comprise actually calculating the angle (429), or may simply be recording a value which is similar or equivalent to the angle (429) such as calculating the resultant distance of dispersion. The process above for computing the dispersion for two rays in a ray pair is then repeated in step (221) until all desired ray pairs have been evaluated and the associated dispersions calculated. When the process repeats, a new first ray (1401) of the first wavelength is originated at the target point (301). Generally the angle and contact point (1402) on the table (21) of new first ray (1401) will be altered in step (223) and as shown in FIG. 3. A new second ray (not shown) and source point (1411) are computed to generate a new ray pair. The steps may be repeated any number of times to create a set of ray pairs where each ray within a ray pair is "sourced" at the same source point (411), (1411) but where different ray pairs will generally not share source points (411), (1411) with each other.

It should be apparent that it is computationally complex to determine the path of the second ray (403) and first ray (401), and that if the second ray (403) and first ray (401) take different paths, the calculated dispersion may not be generalizable across the spectrum between them because some light incident on the spectrum from the same point may follow an entirely different path. Due to these issues, the system, in an embodiment, may simplify the ray tracing to require certain interactions in order to simplify the path taken by the first ray (401) and second ray (403). In particular, the system may require the second ray (403) to interact with the same faces as the first ray (401) in the reverse order. In effect, the second ray (403) is required to follow a reverse path to the path that is taken by the first ray (401). The second ray trace is not identical to the first ray trace, as generally the second ray (403) will be reflected differently from the first ray (401), however, the facets or faces intersected by the second ray (403) will generally be the same as the facets or faces intersected by the first ray (401) even if the points of intersection with those facets or faces is different. Therefore the rays in any ray pair follow the same path, but will generally have different traces if that path from that source diffuses light in the spectrum between and including the two chosen wavelengths.

This provides for simplified computational control because the system can always test for the next face of interaction beginning with the face that would be the appropriate face if the reversed first ray (401) was being used, which is usually close to the point of intersection of the second ray (403) providing for increased computational efficiency. Further, by requiring the second ray (403) to intersect with the same faces, and be sourced from the source point (411) on the second surface (21) and incident on the diamond (20) at the same angle, the combination of the first ray (401) and second ray (403) produces an indication of light of different wavelengths that follows the same path and is dispersed by the interaction with that path. That is, the ray pair shows the dispersion of a particular incident path.

Further, the calculated dispersion corresponds to the actual dispersion by the diamond (20) as seen by the observer as at least one ray (specifically the first ray (401)) passes through the target point (301). The path's dispersion calculated from the ray pair can then be generalized across the spectrum of possible incident light following that path making it more representative of dispersion.

As mentioned above, there is an angular difference in the path of the first ray (401) between the target point (301) and the table (21), and the path of the second ray (403) between the table (21) and the second surface (321) if the path, when taken by light from the source point (411) and incident on the diamond at point (431), is dispersed in the spectrum between and including the chosen wavelengths. This angular difference, therefore, can be used to compute the dispersion of the particular path within the diamond (20) taken by the first ray (401) and second ray (403) from the source point (411). Alternatively, the dispersion distance can be used in the calculation. As the two are mathematically interchangeable, which is selected is irrelevant as either will give similar information. In an embodiment, One of the two different wavelengths can correspond to a wavelength in the blue portion of visible spectrum (e.g., between about 400 nm and 500 nm, such as about 450 nm). The other wavelength can correspond to a wavelength in the red portion of the visible spectrum (e.g., between about 600 nm and 700 nm, such as about 650 nm) to provide dispersion over a wide portion of the spectrum. As an example of such a relatively large difference, the wavelengths of the rays in a ray pair can be 487 nm and 657 nm, respectively.

While the above may be valuable because it includes a broad spectrum indicating that a wide variety of light incident on the diamond (20) from the source point (411) and at the same incidence direction from that source point (411) will act the same way, the difference between the wavelengths of the rays in each ray pair can vary in any manner desired. In other embodiments, the difference between the wavelengths of the rays in each ray pair can be relatively small (e.g., about 1-10 nm). This allows for a better chance that the rays will follow the same path and an accurate determination of dispersion of the path utilizing simpler calculations, without consideration of secondary paths which may be taken by rays of widely different wavelengths, resulting in data that is ungeneralizable to the spectrum and path. For example, in some embodiments, the wavelengths of rays in a ray pair can be 519 nm and 521 nm, respectively. Alternatively, the difference between the wavelengths of the rays in each ray pair can be relatively large (e.g., about 50 nm or more, about 100 nm or more) but may be focused toward a particular portion of the spectrum (for instance the red end, or blue end).

A value for ray dispersion can be calculated for each ray pair in the manner known to those of ordinary skill in the art utilizing mathematical relationships between the first ray (401), second ray (403), and distance (427) from the target point (301) to the intersection point (421) and the point the first ray (401) entered the table (21). However, the dispersion need not be directly calculated. In an alternative embodiment, the distance (427) between the target point (301) and the intersection point (421) or the angle (429) can be used directly as representative of dispersion.

The steps discussed above have provided for dispersion for a single pair of rays. The first ray (401) in the ray pair from the target point (301) and the second ray (403) in the ray pair returned from the source point (411) that was originally intersected by the first ray (401). As discussed above the process can be repeated to generate a large number of ray pairs and associated dispersions which provide for indications of the dispersion of a large number of paths. In an embodiment, ray pairs are gathered for a plurality of first rays (401), (1401) that intersect both the table (21) and target point (301). It is preferred that every first ray (401), (1401) intersecting the target point (301) and table (21) be either measured or assumed to follow an already measured path, so that the fire potential of the entire table (21) or other target portion of the diamond (20) to be evaluated, relative to the target point (301), can be extrapolated. This multitude of paths can comprise either or both of rays traced from the original target point (301) at a plurality of different angles, or rays traced from a variety of different target points.

In general, a sufficient number of rays to provide meaningful data should be traced. In some embodiments, the number of rays traced can be relatively large (e.g., about 100,000 or more, about 500,000 or more, about 1,000,000 or more). For example, in embodiments where one or more maps or drawings of properties of the diamond (20) are to be generated, a sufficiently large number of rays to fill the image, or allow what is considered accurate estimating, should be used. However, in certain embodiments, fewer rays can be traced (e.g., about 50,000 or less, about 20,000 or less, about 5,000 or less, or even as few as 1,000, 100, or 10). For example, when calculating fire potential from a more symmetrical diamond, about 5,000 to about 50,000 rays can provide sufficiently accurate results.

The algorithm can launch the first rays (401), (1401) in different directions from the target point (301) at random or systematically. Typically, the first rays (401), (1401) are launched within a cone or spiral of directions corresponding to the area of the diamond (20) exposed to the target point (301). This can ensure that all rays that are traced contact the diamond, further increasing computational efficiency.

It should be apparent that each of the ray pairs obtained in step (221) comprises a formed ray trace. That is, both rays in the trace have the same point source and are incident toward the user's eye. Dispersion calculated from this forward ray trace is a more accurate indicator of fire as seen by the hypothetical observer.

Once the multitude of ray pairs is obtained in step (221), the ray pairs can now be used to examine the dispersion of the diamond (20) as viewed from the target point (301) in step (225). In an embodiment, this data can comprise raw dispersion calculations (e.g., average angular ray dispersion and/or average positional ray dispersion) for different portions of a diamond (20) or the diamond (20) as a whole. For example, dispersion can be calculated individually for the table (21) or bezel (21). Accordingly, the diamond's (20) fire potential can be evaluated mathematically for different portions of the diamond (20) or the diamond (20) as a whole. As should be apparent, the set of calculated ray pairs shows how white light, from a selected number of point source incidences on the diamond, is dispersed so that the user only sees light of the wavelength of the first ray (401), (1401). However, it should be apparent that even with a large number of ray pairs only a small percentage of the light actually incident on the diamond (20) has been examined and even light from the same source can enter the diamond (20) at a point other than point (431). These alternatives, however, can be generalized to the dispersion calculated for the paths as light following a similar path will generally have a similar dispersion. However, a different portion of the spectrum may be incident on the eye.

To present the fire potential of the diamond (20) to a user, it can be desirable to present both specific dispersions for the different incident paths or to present a simple representation of the dispersion as a whole. In the first case, it is likely that there are such a high number of ray pairs that a more simplified presentation is necessary. In an embodiment, the values of dispersion from the ray pairs can be mapped to a drawing of the diamond's (20) table (21) and crown (29) showing the expected dispersion based on where the first ray (401) originally entered the diamond (20) at the contact point (402). To generate such a map, each particular ray pair's dispersion can be assigned to a preassigned grade range associated with a color or other indicator. This allows a large number of ray pair dispersions to be represented in a relatively straightforward graphical format.

In order to grade or evaluate the diamond (20), the indicator associated with the dispersion of the ray pair may be mapped in a graphical format to a graphical representation or the surface of the table (21), crown (29), or other portion of the surface of the diamond including the contact point (402) where the first ray (401) in the ray pair was incident. In effect, the indicator is placed at the contact point on the representation. This process is repeated for all the different rays, and associated contact points, resulting in a presentation with a large number of indicators showing the general layout of the dispersions. This is a so-called "fire potential map" multiple examples of which are shown in FIG. 4.

Figure 4:
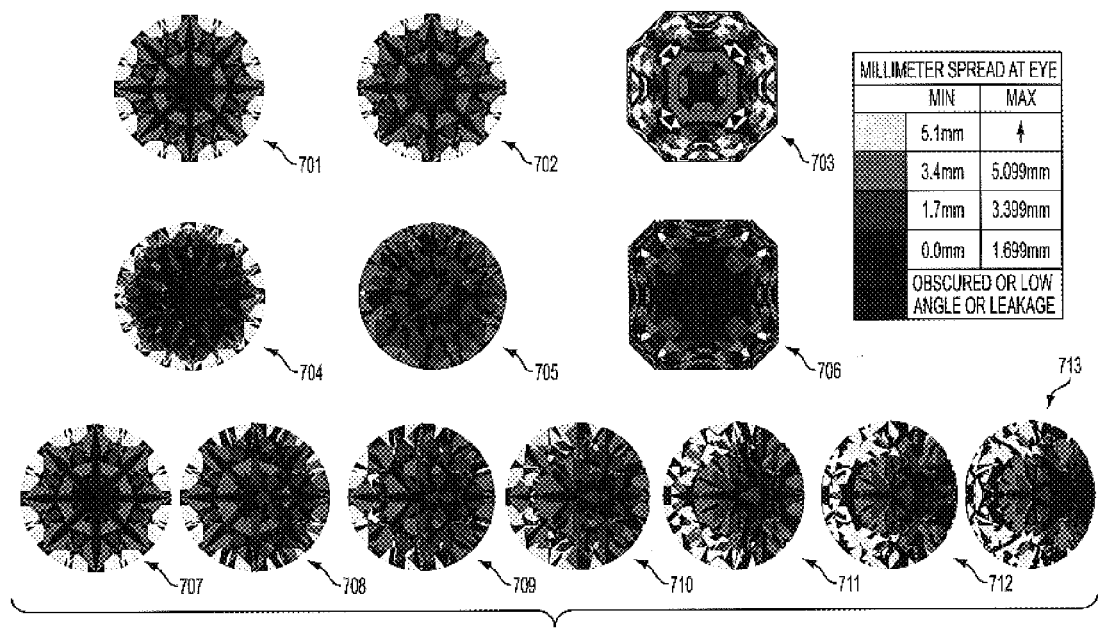
FIG. 4 shows multiple fire potential maps, in color, comparing differently cut diamonds and diamonds arranged in different orientations. The FIG. allows for the fire potentials of different diamonds to be compared.

Because the second surface is a plane, instead of using the dispersion angle to determine the color or evaluate the dispersion, the distance (427) between the target point (301) and intersection point (421) can be used directly and is used in FIG. 4 to show fire potential. There is no need to calculate a dispersion angle (429) as the distance (302) is generally great compared to the diameter of the diamond (20) allowing the distance (427) to be very closely related to the angle. Based on a plane located 25 mm from the table (21), a spread of 5.1 mm or more is generally considered a very high dispersion and would likely be able to show a significant amount of fire. This is indicated by the color yellow in FIG. 4. A spread of 3.4 to 5.099 mm may be considered a high dispersion and is indicated by the color orange in FIG. 4, a spread of 1.7 to 3.399 mm may be considered a moderate dispersion and is represented by the color red in FIG. 4, and a spread of less than 1.699 mm can be considered a low dispersion and is represented by dark red in FIG. 4. Where the same path is not followed by both rays, black is used to show that there is leakage or low angle calculations. These colors are merely exemplary and any colors can be used in other embodiments.

In the fire potential map (500) of FIG. 4, however, the lighter colored areas therefore indicate where the second ray (403) intersects the second surface (321) at a greater distance from the target point (301) indicating greater dispersion while the darker areas progressively show where less and less dispersion is detected. It should be apparent that the diamond (701) a Tolkowsky, cut generally accepted as being ideal; and the diamond (702), a slightly different cut also considered ideal, have a much higher degree of dispersion than the inferior cut (704) which is a poor cut. Diamond (704) is clearly darker having fewer areas of higher dispersion. Diamond (705) is not symmetrical and also poorly cut and in addition to being darker, also does not show the star like pattern of the more symmetrical cuts, but instead is a mish-mash of colors and placements. The pattern of the dispersion which is subjectively attractive in the Tolkowsky cut diamond (701) forming a star like pattern with high contrast is not clear in the inferior cuts (704) and (705). This is even clearer between the ideal Emerald cut (703) and poor Emerald cut (706).

The fire potential rays of FIG. 4 can be further modified to provide additional information. In the depicted embodiment, the ray essentially shows pure dispersion. This can be adjusted mathematically accommodating appearance under variations such as, but not limited to, different types of illumination, illumination distribution, and observer position.

The fire potential map presentation (500) of FIG. 4 is generally the preferred method for providing the fire potential or dispersion of the diamond (20) to an end user. While it is generally expected that a diamond (20) with more areas of higher dispersion will produce more fire and will have more color, simply having more fire potential may not be desirable as it would be to have a diamond (20) with good dispersion generally and good contrast between points of low and high dispersion. The graphical presentation of fire potential map (500) allows a user to compare both objective, and subjective comparisons and also see how good cuts (701), (702) and (703) can result in different appearance. Further, once a user knows what they like in a diamond (20) with regards to dispersion characteristics, they can look for diamonds (20) having similar maps without needing to separately examine each stone under a number of different conditions. Maps 707 through 713 show how an individual diamond can also be displayed at different angles utilizing an array of target points. Map 707 shows the same map as map 701, each consecutive figure then rotates the diamond 5 degrees from the prior map (so, for example, the diamond in map 711 is tilted 20 degrees from the map 707). The use of the array of target points in this layout shows how this ideal cut not only displays fire from directly above, but also from side angles. As an observer will generally have two eyes and neither is truly directly above the center of the table such an array of maps can provide significant information on fire potential.

In a still further embodiment, other graphical representations of fire potential may be used instead of the color maps of FIG. 4. The maps may be represented in grey scale, they may be presented in a graphical format that is not representative of the diamond's table, for instance, in a linear form or in a fixed shape such as, but not limited to, a circle or polygon.

In a still further embodiment, the fire potential may be presented as a single or a few representative indicators or grades. For example, the dispersion values may be combined based on a weighted average for the amount of surface where that level of dispersion is indicated. This average can then be presented as a value for the diamond (20). Alternatively, the values may be placed into groupings which are then represented by a "grade" which could be an alphanumeric or other indicator.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method for evaluating the fire potential of a gemstone, the method comprising;
    generating a representation of the geometry of a gemstone having a table and a plurality of faces;
    defining a target point above said table of said gemstone;
    tracing a first ray of a ray pair having a first wavelength from said target point through said gemstone allowing said first ray to interact with at least a portion of said faces;
    determining a source point at which said first ray intersects a first surface after leaving said gemstone;

tracing a second ray of a ray pair having a second wavelength from said source point and through said gemstone allowing said second ray to interact with at least a portion of said faces;

determining an intersection point at which said second ray intersects a second surface;

calculating a dispersion between said first ray and said second ray;

repeating the above steps for a plurality of ray pairs; and using said dispersions to evaluate the fire potential of said gemstone.

2. The method of claim 1 wherein said gemstone is a diamond.

3. The method of claim 1 wherein said step of calculating comprises determining the distance of said target point to said intersection point.

4. The method of claim 3 wherein said distance is within a predetermined range of distances, said range being one of a plurality of ranges of distances.

5. The method of claim 4 wherein said step of using comprises the steps of:

color coding each of said predetermined ranges in said plurality; providing a graphical view of said table of said gemstone; and mapping said color coding associated with said range associated with said distance on the location of said graphical view of said table that said first ray intersected said table.

6. The method of claim 4 wherein said table is part of a crown and wherein said step of using comprises the steps of color coding each of said predetermined ranges in said plurality; providing a graphical view of said crown of said gemstone; and mapping said color coding associated with said range associated with said distance on the location of said graphical view of said crown that said first ray intersected said table.

7. The method of claim 1 wherein said first ray enters said gemstone through said table.

8. The method of claim 1 wherein said first surface is a hemisphere.

9. The method of claim 1 wherein said second surface is a plane.

10. The method of claim 1 wherein said portion of said faces with which said second ray interacts is the same portion of faces with which said first ray interacts.

11. The method of claim 10 wherein said second ray interacts with said portion of said faces in the opposite order that said first ray interacts with said portion of said faces.

12. A system for evaluating the fire potential of a gemstone the system comprising:

a computer having software running thereon, said software being able to generate a representation of a gemstone in a computer readable form;

an algorithm operating on said computer for tracing a ray through said representation of said gemstone to form a path; and a memory for storing said path;

wherein, a first path is traced for a first ray having a first wavelength and originated at a target point, said first ray also intersecting a first surface at a source point after being traced through said representation;

wherein a second path is traced for a second ray having a second wavelength and originated at said source point, said second ray not intersecting said target point after being traced through said representation;

wherein said computer can calculate a dispersion associated with the ray pair including the first ray and second ray based on said first path and said second path;

wherein said computer can repeat tracing first paths, tracing second paths, and calculating an associated dispersion for a plurality of ray pairs;

wherein said dispersion of said plurality of ray pairs is representative of fire potential of said gemstone; and wherein said computer provides a representation of all said dispersions, said representation indicating the fire potential of said gemstone.

13. The system of claim 12 wherein said gemstone is a diamond.

14. The system of claim 12 wherein said first surface is a hemisphere.

15. The system of claim wherein said representation is alphanumerical.

16. The system of claim 12 wherein said representation is graphical.

17. A method for indicating the fire potential of a gemstone, the method comprising:

providing a graphical representation of at least a portion of a surface of a gemstone;

defining a target point, a plurality of source points and a plurality of contact points, each contact point in said plurality of contact points being on said portion of said surface of said gemstone;

calculating that white light sourced at one of said source points and directed into said gemstone is dispersed a particular distance by said gemstone and that light of a first predetermined wavelength sourced at the same source point and directed into said gemstone follows a first trace which passes through a first of said contact points and through said target point;

selecting at least two different indicators, each of said indicators representing a particular range of distance of dispersion;

recognizing which of said ranges of distances of dispersions includes said distance of dispersion of white light sourced from said first of said source points;

placing said indicator representing said range of distance of dispersions including said distance of dispersion of white light sourced from said first of said source points on said graphical representation at said contact point;

repeating said steps of determining, selecting, recognizing and placing for all of said contact points; and utilizing the resultant graphical representation as an indicator of fire potential of said gemstone.

18. The method of claim 17 wherein said indicators are colors.

19. The method of claim 18 wherein in said step of calculating said particular distance is calculated by generating a ray pair via reverse ray tracing, wherein one of said rays in said ray pair follows said first trace.

20. The method of claim 18 wherein in said step of calculating, said particular distance is calculated by generating a ray pair via forward ray tracing, wherein one of said rays in said ray pair follows said first trace.

* * * * *